(12) United States Patent
Backer et al.

(10) Patent No.: US 9,376,373 B2
(45) Date of Patent: *Jun. 28, 2016

(54) VINYL MONOMERS HAVING CHELATING FUNCTIONALITY

(71) Applicants: Dow Global Technologies LLC, Midland, MI (US); Rohm and Haas Company, Philadelphia, PA (US)

(72) Inventors: Scott Backer, Collegeville, PA (US); Allen Bulick, Bolingbrook, IL (US); Joseph Manna, Collegeville, PA (US); Cynthia Rand, Sanford, MI (US); Jia Xie, Hefei (CN)

(73) Assignee: Rohm and Haas Company Dow Global Technologies LLC

( * ) Notice: Subject to any disclaimer, the term of this patent is extended or adjusted under 35 U.S.C. 154(b) by 0 days.

This patent is subject to a terminal disclaimer.

(21) Appl. No.: 14/819,847

(22) Filed: Aug. 6, 2015

(65) Prior Publication Data

US 2015/0376116 A1    Dec. 31, 2015

Related U.S. Application Data

(63) Continuation of application No. 14/354,614, filed as application No. PCT/US2012/062670 on Oct. 31, 2012, now abandoned.

(60) Provisional application No. 61/553,595, filed on Oct. 31, 2011.

(51) Int. Cl.
*C07C 229/30* (2006.01)
*C07C 229/16* (2006.01)
*C07C 227/18* (2006.01)

(52) U.S. Cl.
CPC ............ *C07C 229/30* (2013.01); *C07C 227/18* (2013.01); *C07C 229/16* (2013.01)

(58) Field of Classification Search
CPC .... C07C 229/30; C07C 229/16; C07C 227/18
USPC ......................................... 560/169; 562/564
See application file for complete search history.

(56) References Cited

U.S. PATENT DOCUMENTS

| | | | |
|---|---|---|---|
| 2,840,603 A | 6/1958 | Mock et al. | |
| 2,910,445 A | 10/1959 | Mock et al. | |
| 2,921,809 A | 1/1960 | Kogstrom | |
| 3,090,771 A | 5/1963 | D Alelio | |
| 3,285,886 A | 11/1966 | Gunderson et al. | |
| 3,331,773 A | 7/1967 | Gunderson et al. | |
| 3,591,405 A | 7/1971 | McCarty | |
| 4,348,848 A | 9/1982 | Denzer | |
| 4,386,006 A | 5/1983 | Harrington | |
| 4,560,492 A | 12/1985 | Curry et al. | |
| 4,659,481 A | 4/1987 | Chen | |
| 4,906,383 A | 3/1990 | Chen et al. | |
| 4,913,880 A | 4/1990 | Chen et al. | |
| 4,931,188 A | 6/1990 | Chen | |
| 5,514,732 A | 5/1996 | Vanderlaan et al. | |
| 5,548,049 A | 8/1996 | Brehm et al. | |
| 5,580,941 A | 12/1996 | Krause et al. | |
| 6,060,040 A | 5/2000 | Tournier et al. | |
| 6,869,537 B1 | 3/2005 | Nambu et al. | |
| 6,875,508 B1 | 4/2005 | Nambu et al. | |
| 2008/0026219 A1 | 1/2008 | Tsushima et al. | |
| 2009/0008224 A1 | 1/2009 | DeGroot | |
| 2011/0120936 A1 | 5/2011 | Escobar et al. | |
| 2011/0183880 A1 | 7/2011 | Yoneda et al. | |
| 2014/0303337 A1* | 10/2014 | Backer ...................... | C02F 5/12 526/312 |

FOREIGN PATENT DOCUMENTS

| | | |
|---|---|---|
| CH | 313159 A | 3/1956 |
| DE | 19732664 A1 | 2/1998 |
| GB | 1215116 A | 12/1970 |
| GB | 1310613 A | 3/1973 |
| JP | 05-287690 | 11/1993 |
| JP | 05-302288 | 11/1993 |
| JP | 05-311194 | 11/1993 |
| JP | 2007248863 A | 9/2007 |
| JP | 2009102526 | 5/2009 |
| WO | 9808585 A1 | 3/1998 |

OTHER PUBLICATIONS

XP002690459, Database Registry, Chemical Abstracts Service, 2012.
XP002690460, Database Registry, Chemical Abstracts Service, 2012.
International Search Report and Written Opinion for PCT/US2012/062670 dated Mar. 5, 2013.

* cited by examiner

*Primary Examiner* — Yong Chu

(57) ABSTRACT

The present invention provides novel polymerizable monomers having chelating functionality and processes to make them. In particular, the novel monomers are ethylenically unsaturated aminocarboxylates and are prepared by reacting ethylenediamine triacetic acid or its salt with an ethylenically unsaturated monomer. The ethyleneically unsaturated monomer may be a polymerizable vinyl monomer selected from (o-, p-, m-)DVBMO, allyl glycidyl ether, and glycidyl (meth) acrylate.

11 Claims, No Drawings

VINYL MONOMERS HAVING CHELATING FUNCTIONALITY

CROSS REFERENCE TO RELATED APPLICATIONS

This application is a continuation of U.S. application Ser. No. 14/354,614, filed Apr. 28, 2014, which is a 35 USC §371 national phase filing of PCT/US2012/062670 filed Oct. 31, 2012, which claims the benefit of U.S. Application No. 61/553,595, filed Oct. 31, 2011, each of which is incorporated herein by reference.

FIELD OF THE INVENTION

The present invention relates to novel polymerizable monomers having chelating functionality and methods to make them. In particular, the novel monomers are ethylenically unsaturated aminocarboxylates and are prepared by reacting ethylenediamine triacetic acid or its salt with an ethylenically unsaturated monomer, such as a polymerizable vinyl monomer.

BACKGROUND OF THE INVENTION

Synthetic detergents typically consist of a dispersant, a builder, and other miscellaneous ingredients such as brighteners, perfumes, anti-redepositon agents and enzymes. The dispersant typically comprises a surfactant and functions to separate dirt, soil and stains from fabric and other substrates. Polyacrylates are well known and commonly used dispersant compounds. The builder binds with and forms a complex with metal cations, such as calcium and magnesium ions found in "hard water," which otherwise interfere with the dispersant activity. Such binding and complex formation is also commonly referred to as "chelating" and compounds capable of such interaction with metal ions are known as "chelating agents."

Phosphates are excellent chelating agents, which is why they were historically used as builders for detergents. However, large amounts of phosphorus were released to streams, rivers, lakes and estuaries, even after wastewater treatment. In natural water bodies, phosphorous acts as a fertilizer, increasing growth of algae and aquatic weeds, which depletes oxygen available for healthy fish and aquatic life, whose numbers then decrease. Consequently, most jurisdictions have limited or banned the use of phosphates in detergents.

In the search for phosphate substitutes, amino carboxylate compounds have been found to be effective chelating agents and, therefore, useful as builders for laundry and automatic dishwashing detergents. For example, U.S. Pat. No. 3,331,773, teaches preparation of water soluble polymers having chelating functionality by grafting water soluble chelating monomers onto water soluble polymers. Diethylenetriamine, ethylenediamine tetraacetic acid, and other polyalkylene polyamine polyacetic acids are identified as examples of chelating monomers suitable for grafting onto water soluble polymers.

U.S. Pat. No. 5,514,732 also describes contact lenses made from water insoluble polymers having chelating functionality. The polymers are made from aminopolycarboxylic acids with a polymerizable olefinic group, as well as a hydrophilic monomer and one or more crosslinking monomer.

U.S. Patent Application No. 2008/00262192 describes an water-soluble polymer having a high chelating performance and clay dispersancy which is made by polymerizing an amino group-containing allyl monomer derived from adding an amine compound, such as iminodiacetic acid (IDA), to an allyl monomer, such as allyl glycidal ether (AGE). Also according to U.S. Patent Application No. 2008/00262192, the amino group-containing allyl monomer may be polymerized with other polymerizable monomers including, without limitation, unsaturated monocarboxylic acid monomers.

U.S. Patent Application No. 2009/0082242 discloses a phosphate free dish washing liquor comprising exfoliated nanoclay, a clay-dispersing polymer, as well as other components including known chelating agents such as nitrilotriacetates (NTA), ethylene diamine tetra acetate (EDTA), propylene diamine tetraacetic acid, (PDTA), ethylene diamine N,N'-disuccinic acid (EDDS) and methyl glycine diacetic acid (MGDA), or their salts.

The present invention provides novel polymerizable monomer compounds which are water soluble and have chelating functionality, as well as polymers made therefrom which shall be useful in aqueous systems for scale inhibition, soil removal, tea destaining, particulate dispersion and metal ion binding.

SUMMARY OF THE INVENTION

The present invention provides an ethylenically unsaturated aminocarboxylate monomer having the following general Structure I:

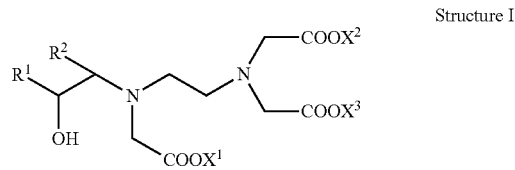

Structure I wherein $X^1$, $X^2$ and $X^3$ are each, independently, hydrogen or a mono- or polyvalent cation and the total charge on the monomer is zero; and one, and only one, of $R^1$ and $R^2$ is an H group, and the other is a polymerizable arm comprising a vinyl group and derived from one or more ethylenically unsaturated monomers. The mono- or polyvalent cation is at least one cation selected from the group consisting of: $Na^+$, $K^+$, $NH_4^+$, organic ammonium ions, $Ca^{2+}$ and $Mg^{2+}$.

In some embodiments, the one or more ethylenically unsaturated monomers comprise a polymerizable vinyl monomer.

In some embodiments, the polymerizable arm may be derived from a divinylbenzene mono epoxide (DVBMO) monomer and have the following structure:

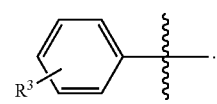

Wherein $R^3$ is a polymerizable ethylenically unsaturated group located at the ortho-, para-, or meta-substituted position of the benzene ring. For example, $R^3$ may be $-CH=CH_2$.

In some embodiments, the polymerizable arm may be derived from an allyl glycidyl ether monomer and have the following structure:

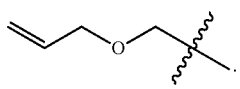 [SMILES: *COCC=C]

In some embodiments, the polymerizable arm may be derived from a glycidyl (meth)acrylate monomer and have the following structure:

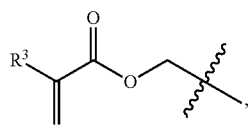

wherein $R^3$ is hydrogen or —$CH_3$.

The present invention also provides a process for preparing the above-described ethylenically unsaturated aminocarboxylate monomer, comprising reacting ethylenediamine triacetic acid or its salt with an ethylenically unsaturated monomer. In some embodiments, the ethylenically unsaturated monomer may comprise a polymerizable vinyl monomer which may be selected from the group consisting of: DVBMO, allyl glycidyl ether, glycidyl (meth)acrylate, and mixtures thereof.

DETAILED DESCRIPTION OF THE INVENTION

All percentages stated herein are weight percentages (wt %), unless otherwise indicated.

Temperatures are in degrees Celsius (° C.), and ambient temperature means between 20 and 25° C., unless specified otherwise.

Weight percentages of monomers are based on the total weight of monomers in the polymerization mixture from which the subject polymer is produced.

"Polymerizable" as used to described a monomer or other molecule means that the monomer or other molecule has at least one carbon-carbon double bond and, therefore, is capable of forming additional covalent bonds with other monomers or molecules of its kind, other polymerizable monomers or molecules, or polymers having polymerizable pendant groups, under normal polymerization conditions, and become incorporated in to the product polymer.

As used herein, the term "(meth)acrylic" includes acrylic acid and methacrylic acid. As used herein, the term "(meth) acrylates" includes esters of acrylic acid and esters of methacrylic acid.

The present invention relates to new monomer compositions which are polymerizable monomers having chelating functionality and are referred to hereinafter as "ethylenically unsaturated aminocarboxylate monomers." The ethylenically unsaturated aminocarboxylate monomers of the present invention have the following general Structure I:

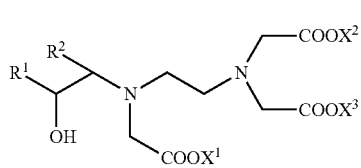

Structure I wherein $X^1$, $X^2$ and $X^3$ are each, independently, hydrogen or a mono- or polyvalent cation and the total charge on the monomer is zero; and one, and only one, of $R^1$ and $R^2$ is an H group, and the other is a polymerizable arm comprising a vinyl group and having one of the following structures:

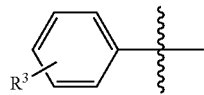

Structure A

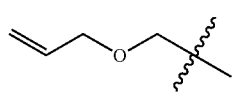

Structure B

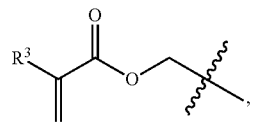

Structure C wherein $R^3$ of Structure A is a polymerizable ethylenically unsaturated group located at the ortho-, para-, or meta-substituted position of the benzene ring. For example, $R^3$ may be —CH=$CH_2$. Hereinafter, abbreviations for the possible structures of DVBMO in the ortho, para, and meta positions are o-DVBMO, p-DVBMO, and m-DVBMO. Note that "(o-, p-, m-)DVBMO" means one or more of the o-DVBMO, p-DVBMO, and m-DVBMO.

Wherein $R^3$ of Structure C is hydrogen or —$CH_3$.

In some embodiments, for example, $X^1$, $X^2$ and $X^3$ of Structure I may each, independently, be at least one cation selected from the group consisting of: $Na^+$, $K^+$, $NH_4^+$, organic ammonium ions, $Ca^{2+}$ and $Mg^{2+}$.

Each of Structures A, B and C are derived from one or more polymerizable vinyl monomers. Structure A may, for example, be derived from a DVBMO monomer, such as o-DVBMO, p-DVBMO, and m-DVBMO, or mixtures thereof. DVBMO has the general structure shown below:

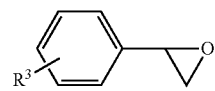

wherein $R^3$ is a polymerizable vinyl (—HC=$CH_2$) group located at the ortho-, para-, or meta-substituted position of the benzene ring.

Structure B may, for example, be derived from an allyl glycidyl ether (AGE) monomer of the following structure:

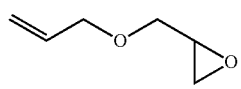

Structure C may, for example, be derived from a glycidyl (meth)acrylate (GA or GMA) monomer of the following structure:

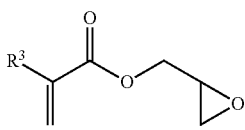

wherein R³ is hydrogen or —CH₃.

The ethylenediamine triacetic acid (ED3A) may, for example, be prepared according to the following reaction equation:

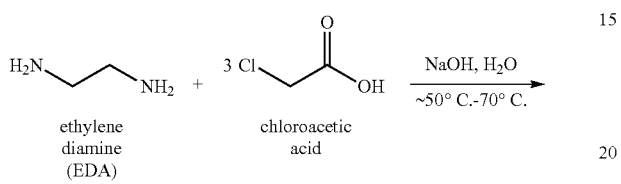

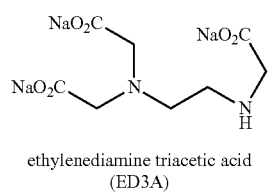

ethylenediamine triacetic acid (ED3A)

The foregoing reaction may be accomplished by reacting ethylene diamine in water, in the presence of sodium hydroxide, with chloroacetic acid at reaction temperatures of 50-70° C. and a pH of 9-10. The total amount of chloroacetic acid to be reacted is added to the ethylene diamine-in-water gradually and continuously over time, such as, over about an hour. The pH of the reaction mixture is maintained at 9-10 by addition of aqueous sodium hydroxide. More specifically, the foregoing reaction will produce a mixed product containing ethylenediamine diacetic acid (ED2A), ethylenediamine triacetic acid (ED3A), and ethylenediamine tetra-acetic acid (EDTA) having the following structures, in approximately the molar proportions indicated:

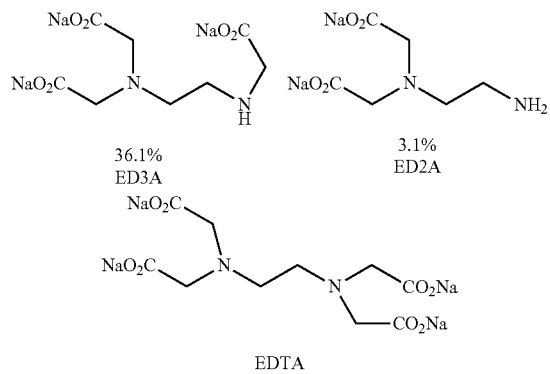

When EDA is reacted with chloroacetic acid at a molar ratio of EDA:chloroacteic acid of 1:2, the product mixture will contain a mixture having molar proportions closer to the following:

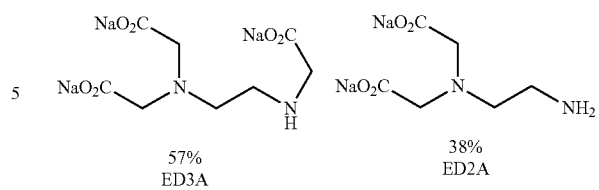

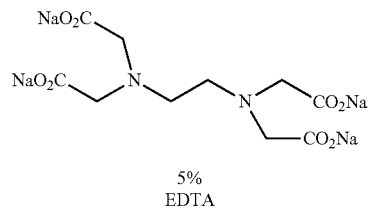

5%
EDTA

It will be noted that the foregoing mixture contains significantly less of the EDTA compound and more of the preferred ED3A and ED2A compounds. As understood by persons of ordinary skill in the relevant art, the EDA-chlororoacteic acid reaction may be further optimized between stoichiometries of 1:2 and 1:3 to maximize the proportion of ED3A contained in the product mixture.

The present invention also provides a process for making the ethylenically unsaturated aminocarboxylate monomers which comprises reacting ethylenediamine triacetic acid (ED3A), or its salt, with a polymerizable vinyl monomer selected from the group consisting of: (o-, p-, m-)DVBMO, allyl glycidyl ether (AGE) and glycidyl (meth)acrylate. This reaction may occur in the presence of a phase transfer catalyst such as, without limitation, benzyltrimethylammonium chloride, tetra-n-butylammonium bromide, methyltrioctylammonium chloride, hexadecyltributylphosphonium bromide, dimethyldiphenylphosphonium iodide, and methyltriphenoxyphosphonium iodide.

The ED3A and vinyl monomer may be reacted in any suitable ratio, as is readily determinable by persons of ordinary skill. The process for making the ethylenically unsaturated aminocarboxylate in accordance with the present invention may be conducted at ambient temperatures.

For example, the particular reaction scheme for the reaction of ED3A with GMA is as follows:

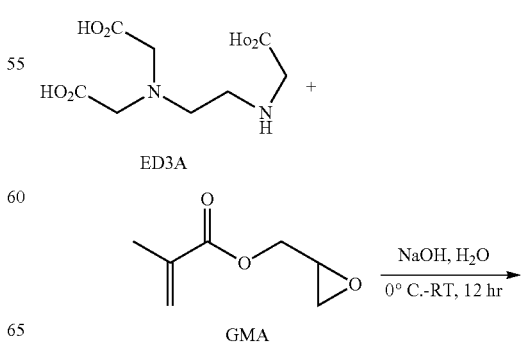

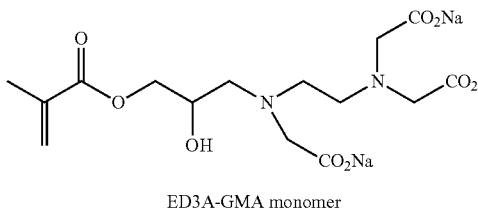

ED3A-GMA monomer

The foregoing reaction produces a mixture of ED3A-GMA monomers having the following structures:

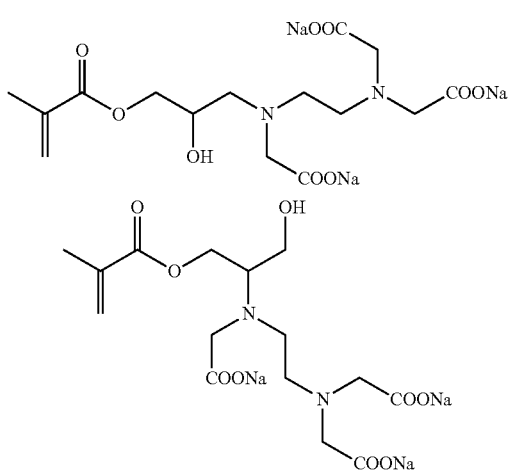

As noted above, the process for producing ED3A will typically produce a mixture of ED3A, ED2A and EDTA. When such a mixture is reacted with the vinyl monomer, the ED2A will also react with the vinyl monomer. For example, when a mixture of ED3A, ED2A and EDTA is reacted with GMA, the product will be a mixture of ethylenically unsaturated aminocarboxylate monomers including those shown above as well as the following structures:

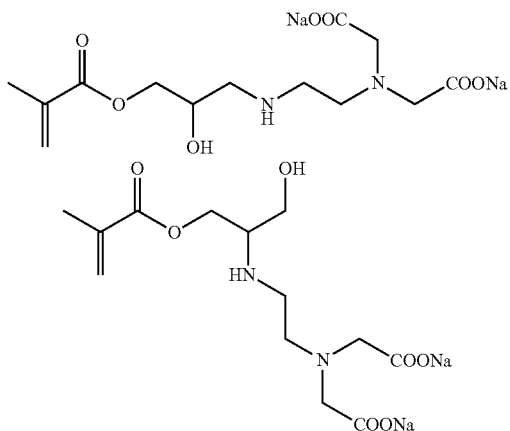

The ED2A-GMA products may be further reacted, with addition chloroacetic acid, to form additional ED3A-GMA monomers in the product mixture, according to the following reaction schemes:

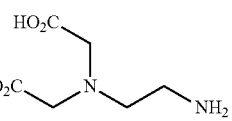

ED2A

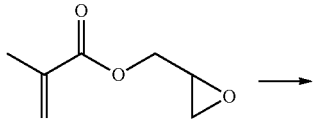

GMA

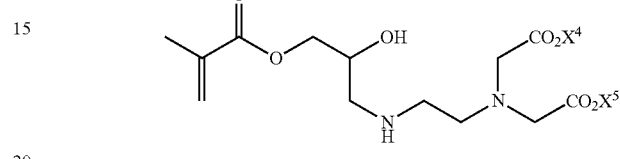

ED2A-GMA monomer

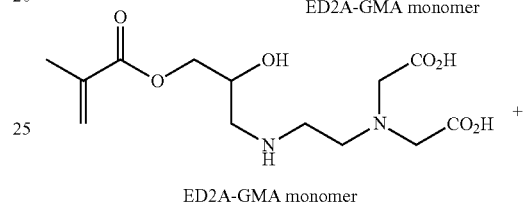

ED2A-GMA monomer

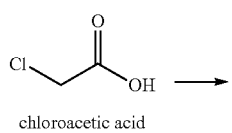

chloroacetic acid

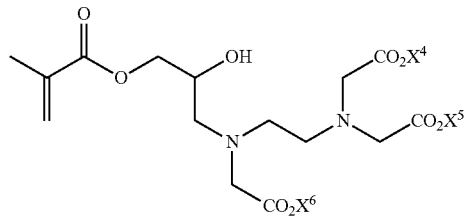

ED3A-GMA monomer $X^4$, $X^5$ and $X^6$ in the structures above may be at least one cation selected from the group consisting of: $Na^+$, $K^+$, $NH_4^+$, organic ammonium ions, $Ca^{2+}$ and $Mg^{2+}$. Thus, upon reacting the mixed product of the EDA-chloroacetic acid reaction with GMA, a mixture of ethylenically unsaturated aminocarboxylate monomers will result which contains all four of the above shown structures of ED2A-GMA and ED3A-GMA. As already mentioned, if desired, further reaction with additional quantities of chloroacetic acid will convert the ED2A-GMA monomer to more of the ED3A-GMA monomer.

As will be readily recognized by persons of ordinary skill in the relevant art, other vinyl monomers, such as AGE or (o-, p-, m-)DVBMO, may be substituted for GMA in the above-described reactions to produce ED3A-AGE or ED3A-(o-, p-, m-)DVBMO monomers according to the present invention. In either case, obviously, persons of ordinary skill will expect that the product will contain the structures shown below, as well as their isomers.

Reaction of ED3A with AGE

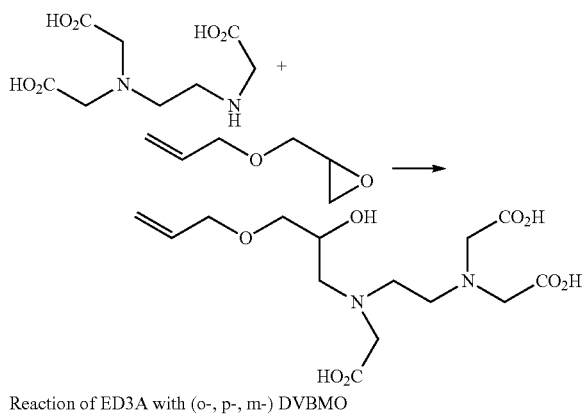

Reaction of ED3A with (o-, p-, m-) DVBMO

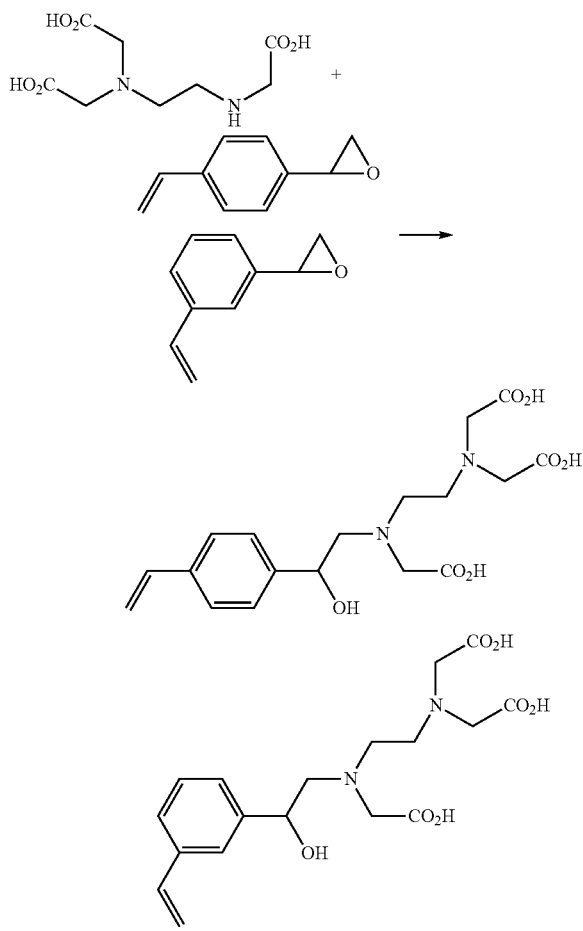

The use, application and benefits of the present invention will be clarified by the following discussion and description of exemplary embodiments of the present invention.

EXAMPLES

Example 1

Synthesis of ED2A, ED3A 2 g ethylene diamine were added to 30 ml DI $H_2O$, followed by addition of 8 g of 50% aqueous NaOH. The ethylene diamine-NaOH solution was raised to 50° C. 9.45 g chloroacetic acid were added to the heated solution over a period of 1 hour. After addition of all the chloroacetic acid, the temperature was raised to 70° C. for 5 hours and the pH was maintained at 9-10 by addition of 50% NaOH throughout the reaction. The resulting product contained the following compounds in the proportions noted: ethylenediamine diacetic acid (3.1%), ethylenediamine tri-acetic acid (36.1%), and ethylenediamine tetra-acetic acid (60.3%).

Example 2

Synthesis of ED3A-GMA Monomer

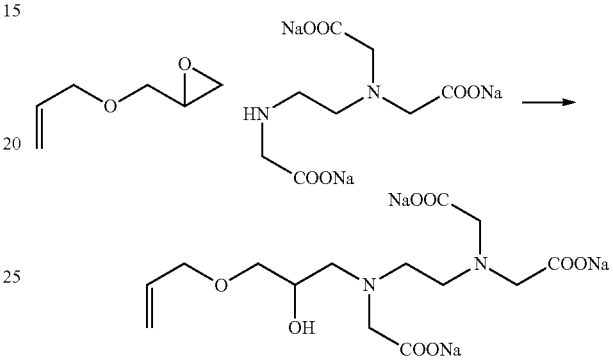

To a 1 L round bottom flask equipped with a magnetic stirbar and an addition funnel, 175 grams of ED3A solution (28.6% active) was charged. The solution was placed in a water bath, and set to stir at a minimum of 300 rpm. 0.4 g of a phase transfer catalyst (benzyltrimethylammonium chloride) was charged to the vessel and allowed to dissolve completely over approximately five minutes. During this time, 18.85 g of allyl glycidyl ether (AGE) was charged to the addition funnel. The AGE was added drop wise to the stirring reaction mass, and when complete, allowed to stir at room temperature until the reaction mass transitioned from two phases to a single phase. This was determined by visual observation, in which prior to completion, the reaction mass was hazy, and would separate into two distinct phases upon termination of stirring. Upon completion, the reaction mass was observed to be a transparent yellow solution, which was stable upon termination of stirring. At this stage the product is a yellow solution of pH 13 and active level of 33.5 wt. % ED3A-AGE. This solution is stable to storage under ambient conditions and can be used as such.

To convert the ED3A-AGE monomer into solid form, sulfuric acid was added drop wise while stirring in order to adjust the pH of the solution, halting the flow of sulfuric acid when the pH was between 7-7.5.

We claim:

1. An ethylenically unsaturated aminocarboxylate monomer having the following general Structure I:

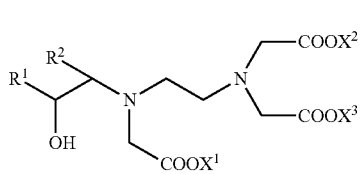

Structure I wherein $X^1$, $X^2$ and $X^3$ are each, independently, hydrogen or a mono- or polyvalent cation and the total charge on the monomer is zero; and one, and only one, of $R^1$ and $R^2$ is an H group, and the other is a polymerizable arm comprising a vinyl group.

2. The ethylenically unsaturated aminocarboxylate monomer according to claim 1, wherein the polymerizable arm has the following structure:

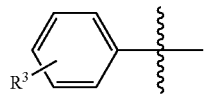

wherein $R^3$ is a polymerizable ethylenically unsaturated group located at the ortho-, para-, or meta-substituted position of the benzene ring.

3. The ethylenically unsaturated aminocarboxylate monomer according to claim 2, wherein $R^3$ is —CH=CH$_2$.

4. The ethylenically unsaturated aminocarboxylate monomer according to claim 1, wherein the polymerizable arm has the following structure:

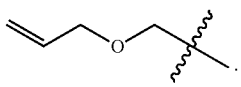 [SMILES: *COCC=C]

5. The ethylenically unsaturated aminocarboxylate monomer according to claim 1, wherein the polymerizable arm has the following structure:

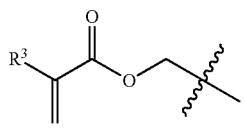

wherein $R^3$ is hydrogen or —CH$_3$.

6. The ethylenically unsaturated aminocarboxylate monomer according to claim 1, wherein the mono- or polyvalent cation is at least one cation selected from the group consisting of: Na$^+$, K$^+$, NH$_4^+$, organic ammonium ions, Ca$^{2+}$ and Mg$^{2+}$.

7. A process for preparing an ethylenically unsaturated aminocarboxylate monomer having the following general Structure I:

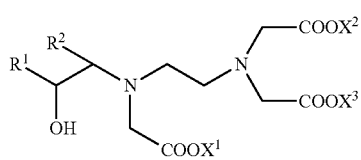

Structure I wherein $X^1$, $X^2$ and $X^3$ are each, independently, hydrogen or a mono- or polyvalent cation and the total charge on the monomer is zero; and one, and only one, of $R^1$ and $R^2$ is an H group, and the other is a polymerizable arm selected from:

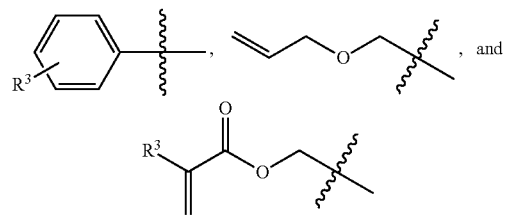

the process comprising reacting ethylenediamine triacetic acid or its salt with a polymerizable vinyl monomer selected from the group consisting of: (o-, p-, m-)DVBMO, allyl glycidyl ether, glycidyl (meth)acrylate, and mixtures thereof.

8. The process according to claim 7, wherein said reacting step occurs in the presence of a phase transfer catalyst.

9. An ethylenically unsaturated aminocarboxylate monomer according to claim 1, having the following structure:

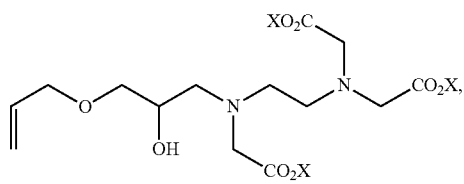

wherein each X is, independently, at least one cation selected from the group consisting of: Na$^+$, K$^+$, NH$_4^+$, organic ammonium ions, Ca$^{2+}$ and Mg$^{2+}$.

10. An ethylenically unsaturated aminocarboxylate monomer according to claim 1, having the following structure:

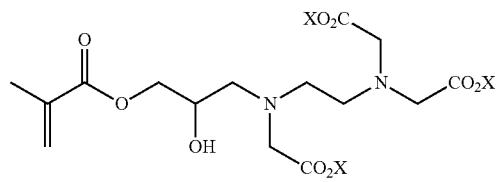

wherein each X is, independently, at least one cation selected from the group consisting of: Na$^+$, K$^+$, NH$_4^+$, organic ammonium ions, Ca$^{2+}$ and Mg$^{2+}$.

11. An ethylenically unsaturated aminocarboxylate monomer according to claim 1, having a structure selected from the group consisting of:

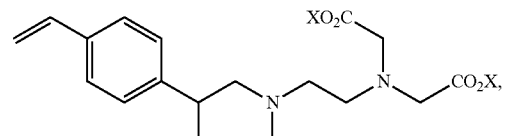

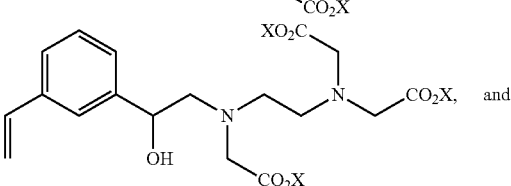

-continued
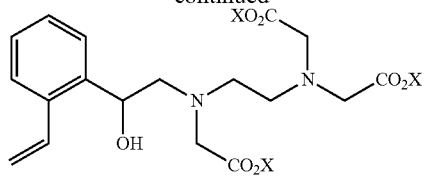
5
wherein each X is, independently, at least one cation selected from the group consisting of: $Na^+$, $K^+$, $NH_4^+$, organic ammonium ions, $Ca^{2+}$ and $Mg^{2+}$.
* * * * *